(12) United States Patent
Perkins

(10) Patent No.: US 8,016,842 B2
(45) Date of Patent: Sep. 13, 2011

(54) METHODS FOR TREATING VULNERABLE PLAQUE

(75) Inventor: D. H. Perkins, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 652 days.

(21) Appl. No.: 12/054,655

(22) Filed: Mar. 25, 2008

(65) Prior Publication Data

US 2009/0248049 A1 Oct. 1, 2009

(51) Int. Cl.
*A61B 17/22* (2006.01)
*A61B 17/32* (2006.01)

(52) U.S. Cl. .......................... 606/159; 606/170

(58) Field of Classification Search .............. 606/159, 606/167, 170, 194; 604/22, 103.05, 506; 600/471
See application file for complete search history.

(56) References Cited

U.S. PATENT DOCUMENTS

| | | | |
|---|---|---|---|
| 4,850,960 A * | 7/1989 | Grayzel | .................. 604/510 |
| 5,830,222 A | 11/1998 | Makower | |
| 6,068,638 A | 5/2000 | Makower | |
| 6,159,225 A | 12/2000 | Makower | |
| 6,190,353 B1 | 2/2001 | Makower et al. | |
| 6,283,951 B1 | 9/2001 | Flaherty et al. | |
| 6,283,983 B1 | 9/2001 | Makower et al. | |
| 6,302,875 B1 | 10/2001 | Makower et al. | |
| 6,375,615 B1 | 4/2002 | Flaherty et al. | |
| 6,379,319 B1 | 4/2002 | Garibotto et al. | |
| 6,419,659 B1 | 7/2002 | Phelps et al. | |
| 6,561,998 B1 | 5/2003 | Roth et al. | |
| 6,579,243 B2 | 6/2003 | Kokate et al. | |
| 6,579,311 B1 | 6/2003 | Makower | |
| 6,660,024 B1 | 12/2003 | Flaherty et al. | |
| 6,669,709 B1 | 12/2003 | Cohn et al. | |
| 6,685,648 B2 | 2/2004 | Flaherty et al. | |
| 6,685,716 B1 | 2/2004 | Flaherty et al. | |
| 6,709,444 B1 | 3/2004 | Makower | |
| 6,726,677 B1 | 4/2004 | Flaherty et al. | |
| 6,746,464 B1 | 6/2004 | Makower | |
| 7,008,411 B1 | 3/2006 | Mandrusov et al. | |
| 7,077,812 B2 | 7/2006 | Naghavi | |

(Continued)

OTHER PUBLICATIONS

Atalar, E. et al., "High Resolution Intravascular MRI and MRS by Using a Catheter Receiver Coil" Magnetic Resonance in Medicine, 36:596-605(1996).

(Continued)

*Primary Examiner* — Anhtuan Nguyen
*Assistant Examiner* — Amy Lang

(57) ABSTRACT

A system and method for treating a vulnerable plaque. The system includes a catheter and a tissue penetrating device for forming at least one opening in an outer wall of a vessel having a vulnerable plaque. An expansion device exerts force on the vulnerable plaque to force core material through the created opening. The system may also include a pocket forming device for forming a pocket in tissue adjacent the outer wall of the vulnerable plaque. The pocket receives the core material expelled through the opening in the outer wall.

15 Claims, 21 Drawing Sheets

U.S. PATENT DOCUMENTS

| | | |
|---|---|---|
| 7,189,250 B2 | 3/2007 | DoBrava et al. |
| 7,195,599 B2 | 3/2007 | Carney et al. |
| 7,288,244 B2 | 10/2007 | Van Langenhove et al. |
| 7,297,154 B2 | 11/2007 | Tu et al. |
| 7,313,432 B2 | 12/2007 | Tearney |
| 2003/0130672 A1* | 7/2003 | DoBrava et al. ............... 606/159 |
| 2005/0075574 A1 | 4/2005 | Furnish et al. |
| 2005/0232965 A1 | 10/2005 | Folatico |
| 2006/0271154 A1 | 11/2006 | Woodall |
| 2007/0076212 A1 | 4/2007 | Zuluaga |
| 2007/0100320 A1* | 5/2007 | Seward et al. ............... 604/506 |
| 2007/0166231 A1 | 7/2007 | Agah |

OTHER PUBLICATIONS

Rivas, P. et al., "In Vivo Real-Time Intravascular MRI" Journal of Cardiovascular Magnetic Resonance 4(2); 223-232 (2002).

Susil, R. et al. "Intravascular Extended Sensitivity (IVES)MRI Antennas" Magnetic Resonance in Medicine, 50:383-390 (2003).

Hamdan, A., et al. "Imaging of Vulnerable Coronary Artery Plaques" Catheterization and Coronary Artery Interventions 70:65-74 (2007).

* cited by examiner

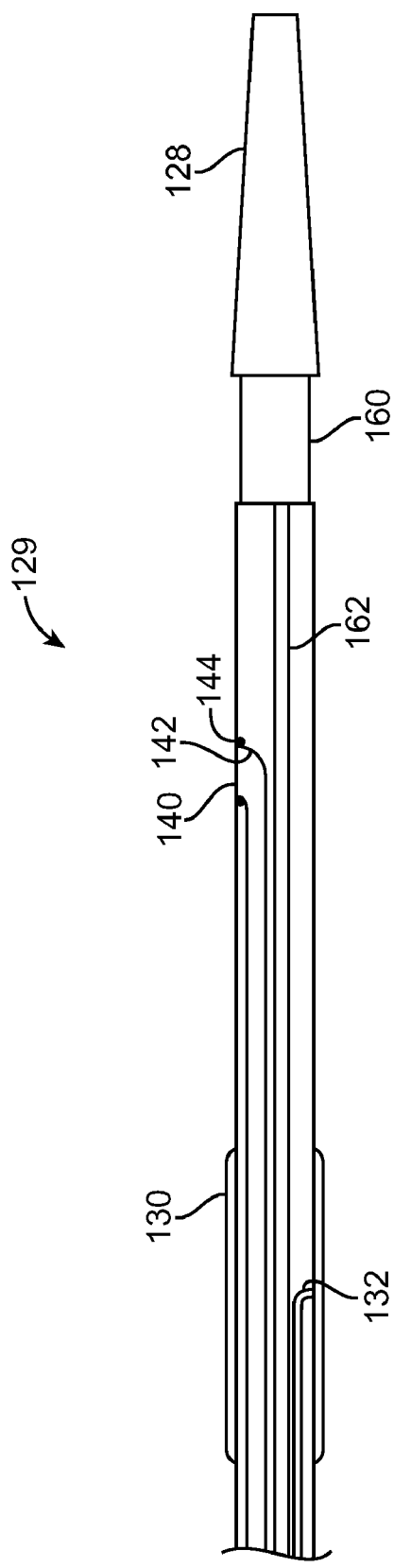
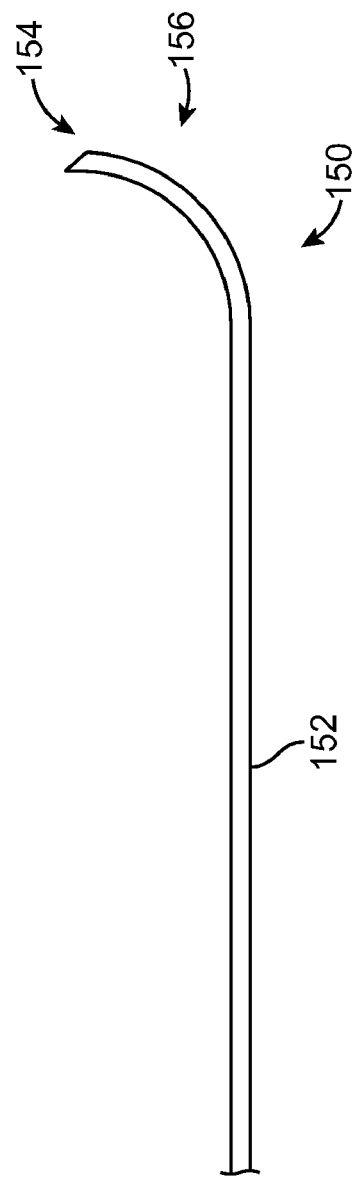
FIG. 2
FIG. 3

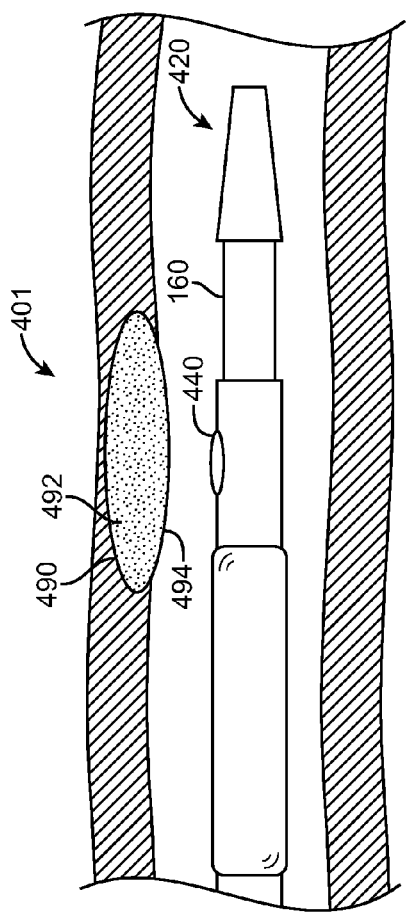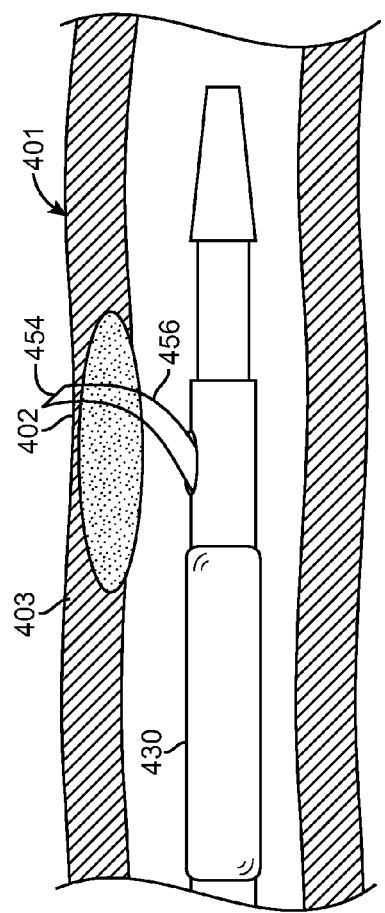

METHODS FOR TREATING VULNERABLE PLAQUE

TECHNICAL FIELD OF THE INVENTION

The present invention relates generally to the field of vascular therapies. More particularly, the invention relates to methods for treating vulnerable plaque.

BACKGROUND OF THE INVENTION

Heart disease, specifically coronary artery disease (CAD), is a major cause of death, disability, and healthcare expense. Until recently, most heart disease was considered primarily the result of a progressive increase of hard plaque in the coronary arteries. This atherosclerotic disease process of hard plaques leads to a critical narrowing (stenosis) of the affected coronary artery and produces anginal syndromes, known commonly as chest pain. The progression of the narrowing reduces blood flow, triggering the formation of a blood clot. The clot may choke off the flow of oxygen rich blood (ischemia) to heart muscles, causing a heart attack. Alternatively, the clot may break off and lodge in another organ vessel such as the brain resulting in a thrombotic stroke.

Within the past decade or so, evidence has emerged expanding the paradigm of atherosclerosis, coronary artery disease, and heart attacks. While the build up of hard plaque may produce angina and severe ischemia in the coronary arteries, clinical data suggests that the rupture of sometimes non-occlusive, vulnerable plaques causes the vast majority of heart attacks. The rate is estimated as high as 60-80 percent. In many instances vulnerable plaques do not impinge on the vessel lumen, rather, much like an abscess they are ingrained under the arterial wall.

The majority of vulnerable plaques include a lipid pool, necrotic smooth muscle (endothelial) cells, and a dense infiltrate of macrophages contained by a thin fibrous cap, some of which are two micrometers thick or less. The lipid pool is believed to be formed as a result of pathological process involving low density lipoprotein (LDL), macrophages, and the inflammatory process. The macrophages oxidize the LDL producing foam cells. The macrophages, foam cells, and associated endothelial cells release various substances, such as tumor necrosis factor, tissue factor, and matrix proteinases. These substances can result in generalized cell necrosis and apoptosis, pro-coagulation, and weakening of the fibrous cap. The inflammation process may weaken the fibrous cap to the extent that sufficient mechanical stress, such as that produced by increased blood pressure, may result in rupture. The lipid core and other contents of the vulnerable plaque (emboli) may then spill into the blood stream thereby initiating a clotting cascade. The cascade produces a blood clot (thrombosis) that potentially results in a heart attack and/or stroke. The process is exacerbated due to the release of collagen and other plaque components (e.g., tissue factor), which enhance clotting upon their release.

Given the prevalence of vulnerable plaque, strategies are continuously being developed for detection and treatment. Several endovascular strategies have been developed for the detection (e.g., diagnosis and localization) of vulnerable plaques. One strategy involves the measurement of temperature within a blood vessel. A localized increase in temperature is generally associated with the vulnerable plaque because of the tissue damage and inflammation. It has been observed that the inflamed necrotic core of the vulnerable plaque maintains a temperature of one or more degrees Celsius higher than that of the surrounding tissue. Measurement of these temperature differences within the blood vessel may provide means for locating vulnerable plaque.

Another detection strategy involves labeling vulnerable plaque with a marker and subsequent detection with an endovascular device. The marker substance may be specific for a component and/or characteristic of the vulnerable plaque. The marker having an affinity for the vulnerable plaque, more so than for healthy tissue. Detection of the marker allows detection of the vulnerable plaque.

Regardless of the strategy used for detection, a formidable problem remains in the treatment of the vulnerable plaque. Without appropriate treatment, the vulnerable plaque may rupture and subsequently release embolic material and cause great risk to the patient, especially when the patient is not in a clinical setting. Drug and other therapies exist that may reduce the size and chance of vulnerable plaque rupture over a relatively long time frame. Percutaneous transluminal coronary angioplasty (PTCA), which is commonly used to treat hard plaques, is contraindicated. In the PTCA procedure, a catheter having an inflatable balloon at its distal end is introduced into the coronary artery, and the balloon is inflated to flatten the hard plaque against the arterial wall. Inflation of a balloon catheter near a vulnerable plaque lesion could rupture the thin fibrous cap that covers the lipid pool, resulting in precisely the clotting cascade that treatment would seek to prevent.

Thickening of the inner wall of a vessel is clearly an unwanted and deleterious side effect when treating hard plaques. However, such thickening could have a positive effect when it serves to strengthen the thin fibrous cap found atop a vulnerable plaque lesion. With the lesion thus stabilized, time is provided for the use of statin drugs or other agents to shrink or remove the lipid pool. These therapies, however, may not be desirable or effective for all patients, including those having vulnerable plaques on the immediate verge of rupture. With such therapies, accidental or unanticipated rupture of these truly vulnerable plaques may occur in a non-clinical setting. Therefore, it would be desirable to provide a treatment strategy that would provide relatively immediate treatment of the vulnerable plaque within a clinical setting. Furthermore, it would be desirable for such a treatment strategy to prevent any embolic material from escaping and causing risk to the patient.

Accordingly, it would be desirable to provide a strategy for treating vulnerable plaque that would overcome the aforementioned and other disadvantages.

SUMMARY OF THE INVENTION

A system and method for treating a vulnerable plaque is described. One embodiment of the system includes a catheter and a tissue penetrating device for forming at least one opening in an outer wall of a vessel having a vulnerable plaque. An expansion device exerts force on the vulnerable plaque to force core material through the created opening.

Another embodiment of the system also includes a pocket forming device for forming a pocket in tissue adjacent the outer wall of the vulnerable plaque. The pocket receives the core material expelled through the opening in the outer wall.

The foregoing and other features and advantages of the invention will become further apparent from the following detailed description of the presently preferred embodiments, read in conjunction with the accompanying drawings. The drawings are not necessarily drawn to scale. The detailed description and drawings are merely illustrative of the inven-

BRIEF DESCRIPTION OF THE DRAWINGS

FIG. 2 illustrates a detailed portion of a cross section of a distal end of one embodiment of a system for treating a vulnerable plaque, in accordance with the present invention;

FIG. 3 illustrates one embodiment of a tissue penetration device for use in the system of FIG. 1, in accordance with the present invention;

FIGS. 4A to 4D illustrates one embodiment of a method of treating a vulnerable plaque using the system illustrated in FIG. 1, in accordance with the present invention;

DESCRIPTION OF THE PRESENTLY PREFERRED EMBODIMENTS

Embodiments of the invention will now be described by reference to the figures wherein like numbers refer to like structures. The terms "distal" and "proximal" are used herein with reference to the treating clinician during the use of the system for treating vulnerable plaque: "distal" indicates a portion of the system for treating vulnerable plaque distant from, or a direction away from the clinician and "proximal" indicates a portion of the system for treating vulnerable plaque near to, or a direction towards the clinician. As defined herein, the deployment site is the axial position in a vessel at which the distal end of a system for treating vulnerable plaque is to be located when a treatment device is deployed.

Figure 1:
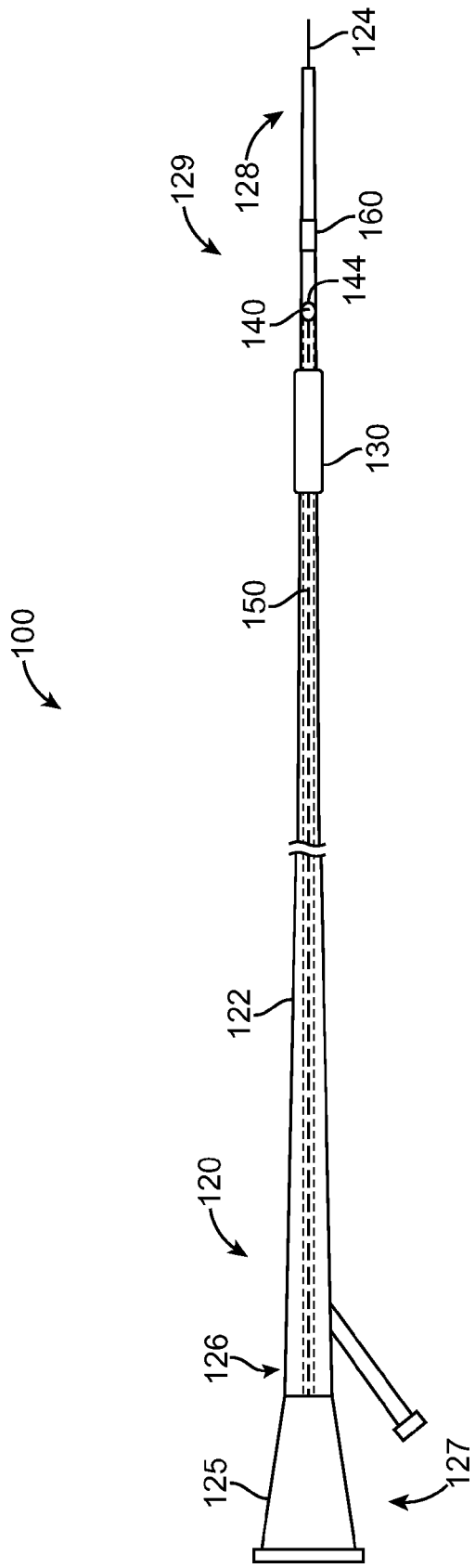
FIG. 1 illustrates a side view of a transvascular catheter system for treating a vulnerable plaque, in accordance with the present invention.

FIG. 1 illustrates a side view of a transvascular catheter system 100 for treating a vulnerable plaque, in accordance with the present invention. System 100 includes a catheter 120, a compression device 130 operably attached to the catheter 120, a side port 140 and a tissue penetrating device 150. In one embodiment, system 100 further includes an imaging device 160.

Catheter 120 is an elongated tubular member defining a circumference or periphery 122 and a longitudinal axis 124 between proximal and distal ends 126, 128, respectively. Catheter 120 includes proximal portion 127 and a distal portion 129 having a size and shape to facilitate insertion into a blood vessel.

In one embodiment, catheter 120 includes an elongated tubular member manufactured from one or more polymeric materials, sometimes in combination with metallic reinforcement. In some applications (such as smaller, more tortuous arteries), it is desirable to construct the catheter from very flexible materials to facilitate advancement into intricate access locations. Numerous over-the-wire, rapid-exchange, and other catheter designs are known and may be adapted for use with the present invention. Catheter 120 can be secured at its proximal end 127 to a suitable Luer fitting 125, and can include a rounded or tapered distal end 128 to reduce harmful contact with a vessel and to facilitate entry into the vessel. In one embodiment, catheter 120 includes a handle at proximal end 127 for actuating various features of system 100 such as for example, the tissue penetrating device 150. Catheter 120 can be manufactured from a material such as a thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, Pebax® resin, Vestamid® nylon, Tecoflex® resin, Halar® resin, Hyflon® resin, Pellathane® resin, combinations thereof, and the like. In one embodiment, catheter 120 includes a lumen and an aperture formed at the distal end 128 allowing advancement over a guidewire.

In one embodiment, compression device 130 comprises an expandable balloon. Balloon 130 can be any variety of balloon, other device capable of expansion (i.e., by filling with a fluid) or stent. Balloon 130 can be manufactured from any sufficiently elastic material such as polyethylene, polyethylene terephthalate (PET), nylon, or the like. Referring to FIG. 2, system 100 includes an inflation lumen 132 for fluid communication between balloon 130 and a fluid source (not shown). In one embodiment, balloon 130 is positioned proximal to side port 140. In another embodiment, system 100 does not include a balloon 130. In one embodiment, balloon 130, or other expansion device used in the performance of the methods for treating a vulnerable plaque described below, is located on a separate catheter. Those with skill in the art will appreciate that system 100 may include compression devices other than a balloon.

One embodiment of system 100 includes an imaging device 160 for imaging the vessel and for locating a vulnerable plaque within the vessel. In one embodiment, imaging device 160 aids in properly orienting side port 140 adjacent the vulnerable plaque identified for treatment. In one embodiment, imaging device 160 is an intravascular ultrasound (IVUS) device disposed within imaging lumen 162. Imaging lumen 162 extends through the catheter 120 from an entry port in the handle to the distal portion 129 for receiving the imaging element 160. A conventional ultrasound transducer is provided on the distal end 129 of catheter 120 and is oriented towards an imaging plane substantially normal to the longitudinal axis 124. The ultrasound transducer or a reflector on the IVUS device 160 (not shown) rotatable about the longitudinal axis 124 provides ultrasonic image slices along the imaging plane in a conventional manner, or alternatively, a phased array of ultrasound transducers may be provided to allow imaging along a plane substantially normal to the longitudinal axis 124, as will be appreciated by those skilled in the art. Those with skill in the art will also appreciate that the invention contemplates the use of other imaging devices for locating and imaging a treatment area having a vulnerable plaque. Numerous methods are known in the art for locating vulnerable plaque. Examples include, but are not limited to, devices that detect localized changes in temperature, pH, and/or inflammation.

System 100 may also include at least one radiopaque marker to aid in the proper orientation of side port 140 toward the vulnerable plaque to be treated. In one embodiment, the opening for side port 140 is defined by a radiopaque material 144 visible by a fluoroscopic imaging system. The marker(s) can be manufactured from a number of materials used for visualization in the art including radiopaque materials such as platinum, gold, tungsten, metal, metal alloy, and the like. Marker(s) can be visualized by fluoroscopy, IVUS, and other methods known in the art.

Referring to FIGS. 2 and 3, illustrated is a detail of distal end 129 of system 100 (FIG. 2) and tissue penetrating device 150 (FIG. 3), in accordance with the present invention.

In one embodiment, tissue penetrating device 150 includes an elongate tubular body 152 having a tissue penetrating portion 156 including a puncturing distal tip 154. Tissue penetrating device 150 may be a solid puncturing element or may be hollow to form a fluid delivery lumen or tissue aspiration lumen. A proximal end of tissue penetrating device 150 extends to proximal end 126 for control by the clinician. In one embodiment, tissue penetrating device 150 is formed from a shape memory alloy, such as Nitinol. In one embodiment, tissue penetrating portion 156 is pre-curved to enhance transverse deployment of the distal tip 154. In this embodiment, the pre-curved tissue penetrating portion 156 is constrained by lumen 142 during delivery. Tissue penetrating portion 156 assumes the pre-curved shape upon release from side port 140.

Tissue penetrating device 150 is inserted into a needle entry port at proximal end 126 and directed distally through the needle lumen 142. In one embodiment, tissue penetrating device 150 is actuated using a thumb slide (not shown) located at proximal end 126. The thumb slide controls axial movement of the tissue penetrating device 150.

Figure 6A:
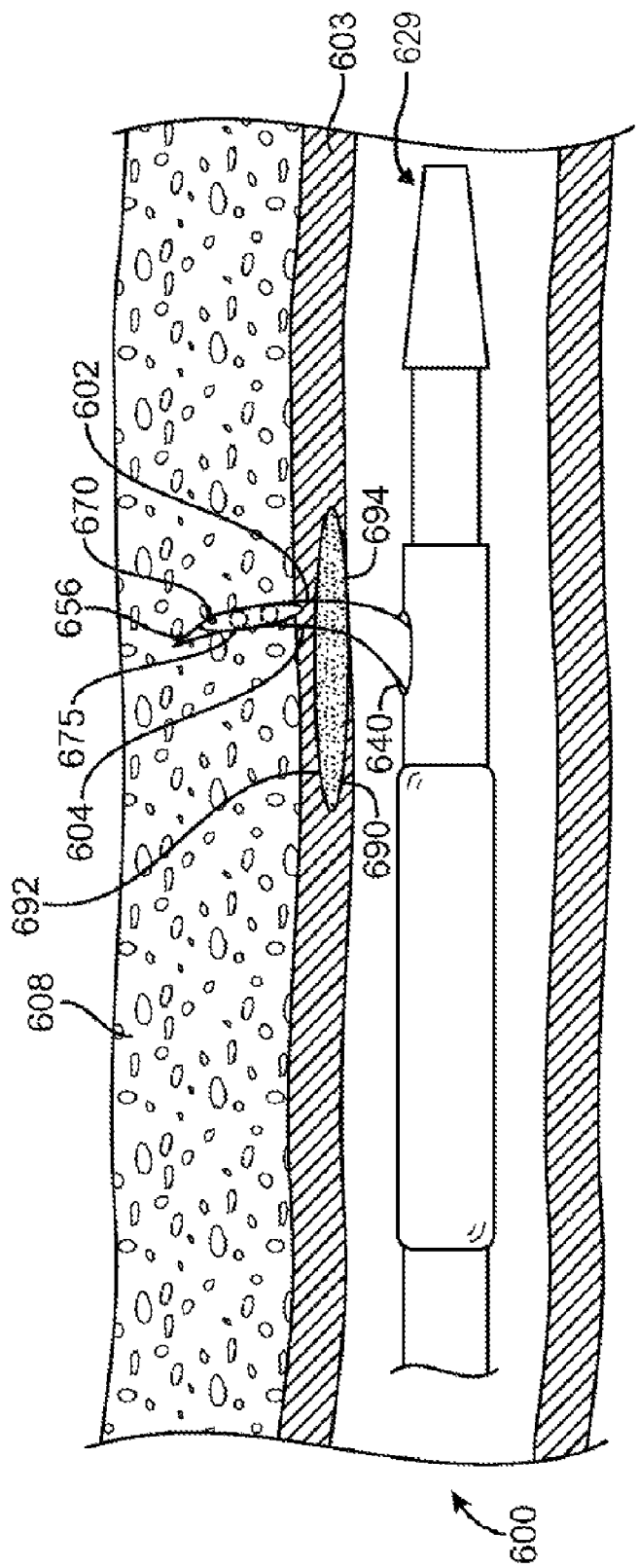
FIGS. 6A to 6D illustrates another embodiment of a method of treating a vulnerable plaque using the system illustrated in FIG. 1, in accordance with the present invention.

In one embodiment, tissue penetrating device 150 includes a lumen for delivering fluid to distal tip 154 and/or tissue penetrating portion 156. In another embodiment, tissue penetrating device 150 includes a lumen for coring and aspiration of the tissue. As described in more detail below, tissue penetrating portion 156 may include a plurality of openings having a predetermined outlet pattern for delivering fluid to an expandable pocket forming device or directly to a portion of tissue adjacent the tissue penetrating portion 156. For example, in one embodiment, tissue penetrating portion 656 includes a closed tip and one or more side openings 675 for inflating an expandable pocket forming device 670 (FIG. 6A). In another embodiment, tissue penetrating portion 756 includes a closed tip and one or more side openings 775 for directing a pocket forming fluid substantially laterally from the tissue penetrating portion 756 into the tissue region 780.

Methods for treating a vulnerable plaque in accordance with the present invention will now be described with reference to FIGS. 4A to 11. The various methods will be described using a vulnerable plaque treatment system, such as system 100 illustrated in FIGS. 1-3, described above.

Figure 4C:
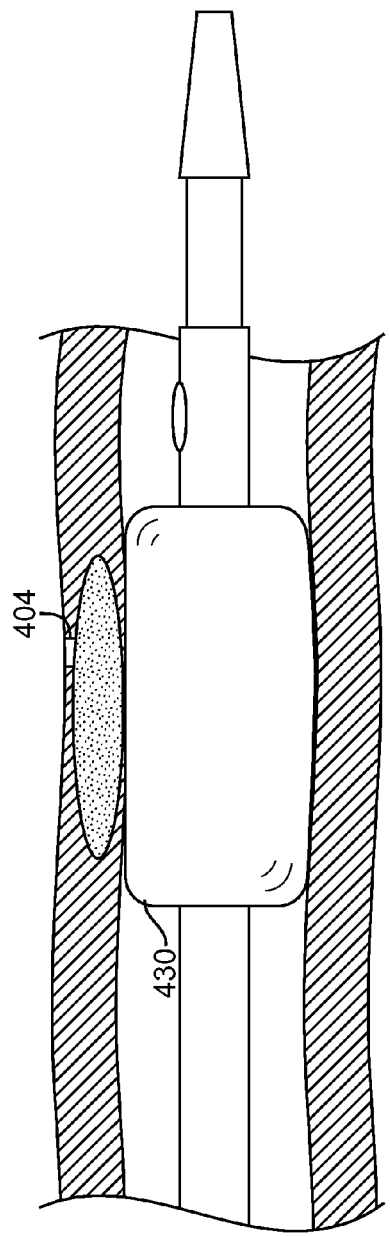
Figure 4D:
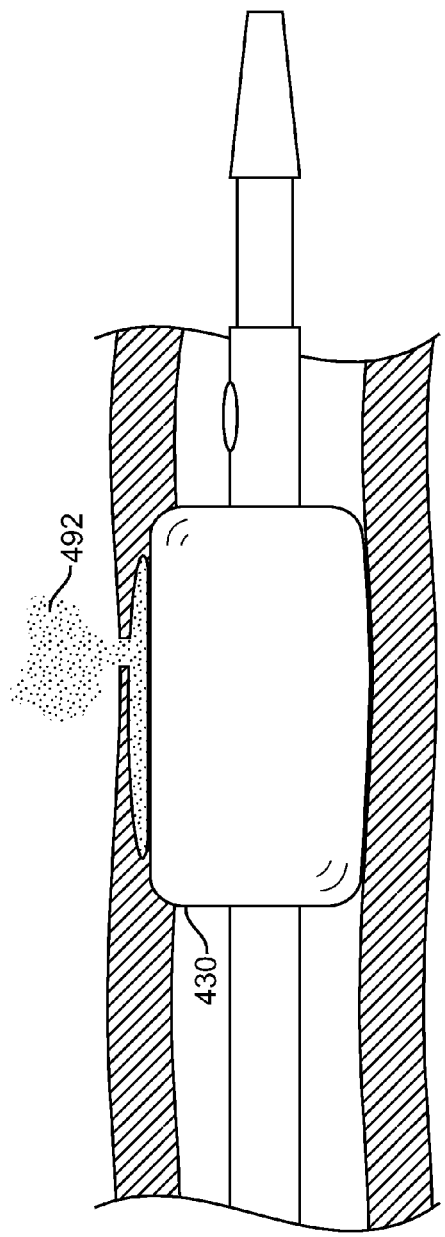
Figure 10:
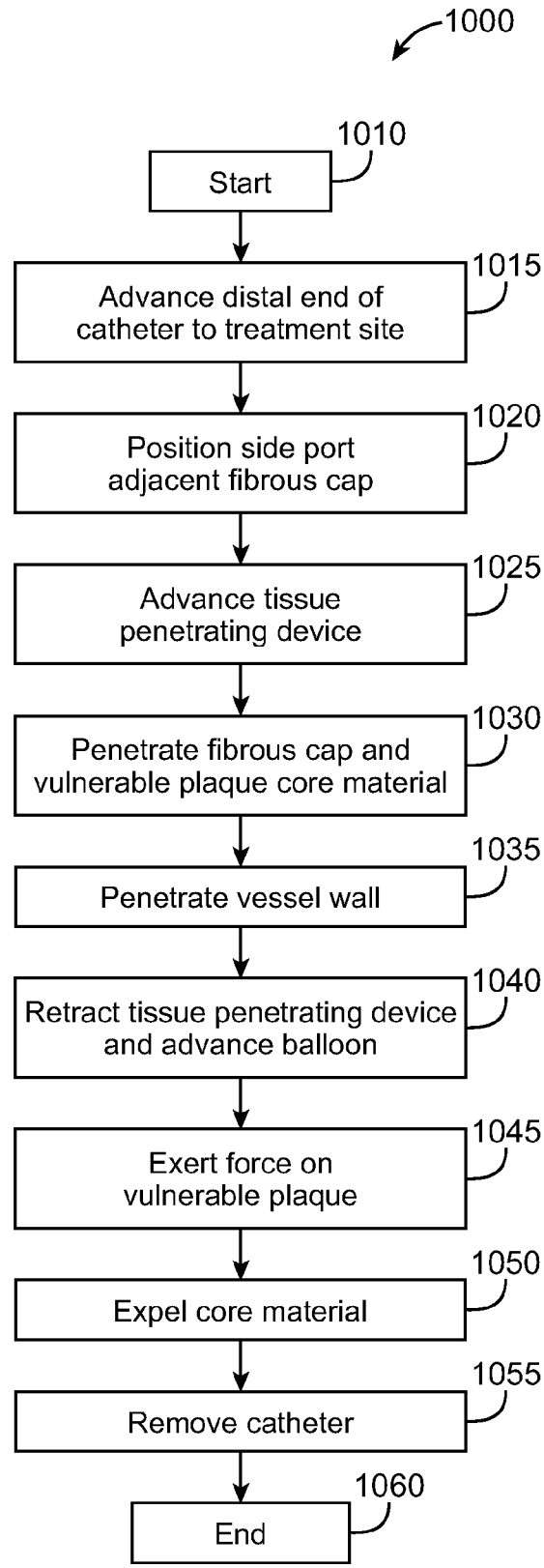
FIG. 10 illustrates a flowchart of a method of treating a vulnerable plaque, in accordance with one embodiment of the present invention.

FIGS. 4A to 4D graphically illustrate one embodiment of a method 1000 for treating a vulnerable plaque, in accordance with the present invention. FIG. 10 is a flow chart for method 1000. FIGS. 4A to 4D illustrate a method of treating a vulnerable plaque located in a wall of a vessel that is not adjacent to a portion of tissue. Method 1000 begins at step 1010. As shown in FIG. 4A, a distal end of a treatment catheter 420 having a tissue penetrating device is advanced to a treatment site within vessel 401 (Block 1015). The treatment site and the vulnerable plaque may be located and visualized using imaging device 160. After determining the location of the vulnerable plaque, side port 440 is oriented towards the fibrous cap 494 of vulnerable plaque 490 having core material 492 (Block 1020). In one embodiment, at least one radiopaque marker disposed on catheter 420, may be used to allow in situ visualization and proper advancement, positioning, and deployment of the tissue penetrating device.

Next, tissue penetrating device is distally advanced to deploy tissue penetrating portion 456 out of side port 440 (Block 1025) to penetrate the fibrous cap 494 and core material 492 (Block 1030). Tissue penetrating device 450 is further advanced so that tissue penetrating portion 456 penetrates an outer portion 402 of vessel wall 403 (Block 1035) to create vessel wall opening 404 or pocket. The pocket is formed in a variety of ways including the aspiration of the material from the vessel wall into the hollow tissue penetrator or the tissue is moved aside due to the penetration of the tissue penetrator or the tissue is expanded by the infusion of fluid into the fluid space by a tissue penetrator with side holes.

At Block 1040, tissue penetrating device 450 is retracted into catheter 420 and the catheter is distally advanced within the vessel to position balloon 430 adjacent the fibrous cap. Next, balloon 430 is inflated to exert pressure on the fibrous cap 494 (Block 1045), shown in FIG. 4C. The pressure exerted on fibrous cap 494 forces the core material contained within the vulnerable plaque out vessel wall opening 404 within outer portion 402 of vessel wall 403. The core material is expelled through opening 404 and into an area adjacent the treated vessel to be absorbed or otherwise disposed of by the body (Block 1050). The expulsion of the core material into the surrounding body may be visualized using an imaging device. Upon release of the core material, the balloon is deflated and the catheter is removed from the body or advanced to another treatment site as determined by the clinician (Block 1055). Method 1000 ends at 1060 and may be repeated as necessary.

Figure 11:
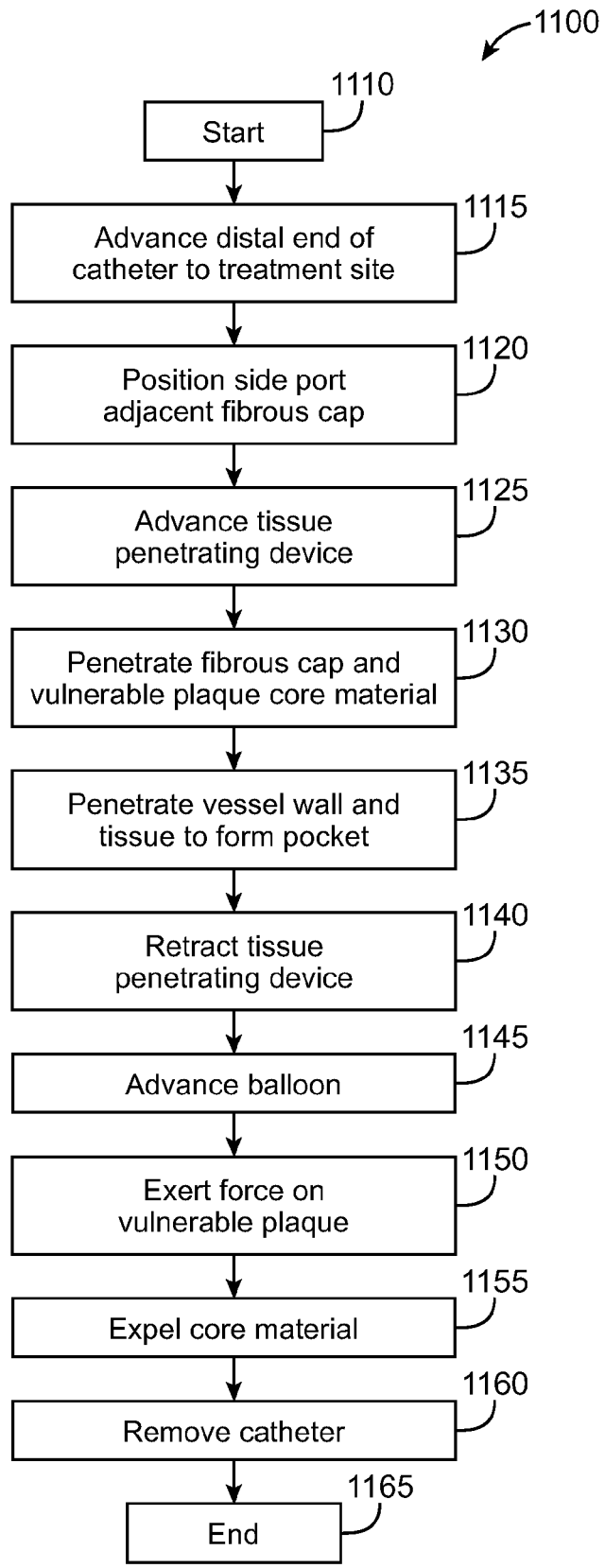
FIG. 11 illustrates a flowchart of another method of treating a vulnerable plaque, in accordance with one embodiment of the present invention.

FIG. 11 is a flow chart for another embodiment of a method 1100 for treating a vulnerable plaque. FIGS. 5A to 5F, 6A to 6D and 7A to 7D graphically illustrate various embodiments of method 1100. As described below in more detail, each of the series of figures graphically illustrate a method treating a vulnerable plaque wherein at least one pocket is formed in tissue adjacent to a vessel having a vulnerable plaque.

FIGS. 5A to 5F graphically illustrate one embodiment of a method 1100 for treating a vulnerable plaque, in accordance with the present invention. FIG. 11 is a flow chart for method 1100. FIGS. 5A to 5F illustrate a method of treating a vulnerable plaque located in a wall of a vessel that is within or adjacent to a portion of tissue. Method 1100 begins at step 1110.

Figure 5A:
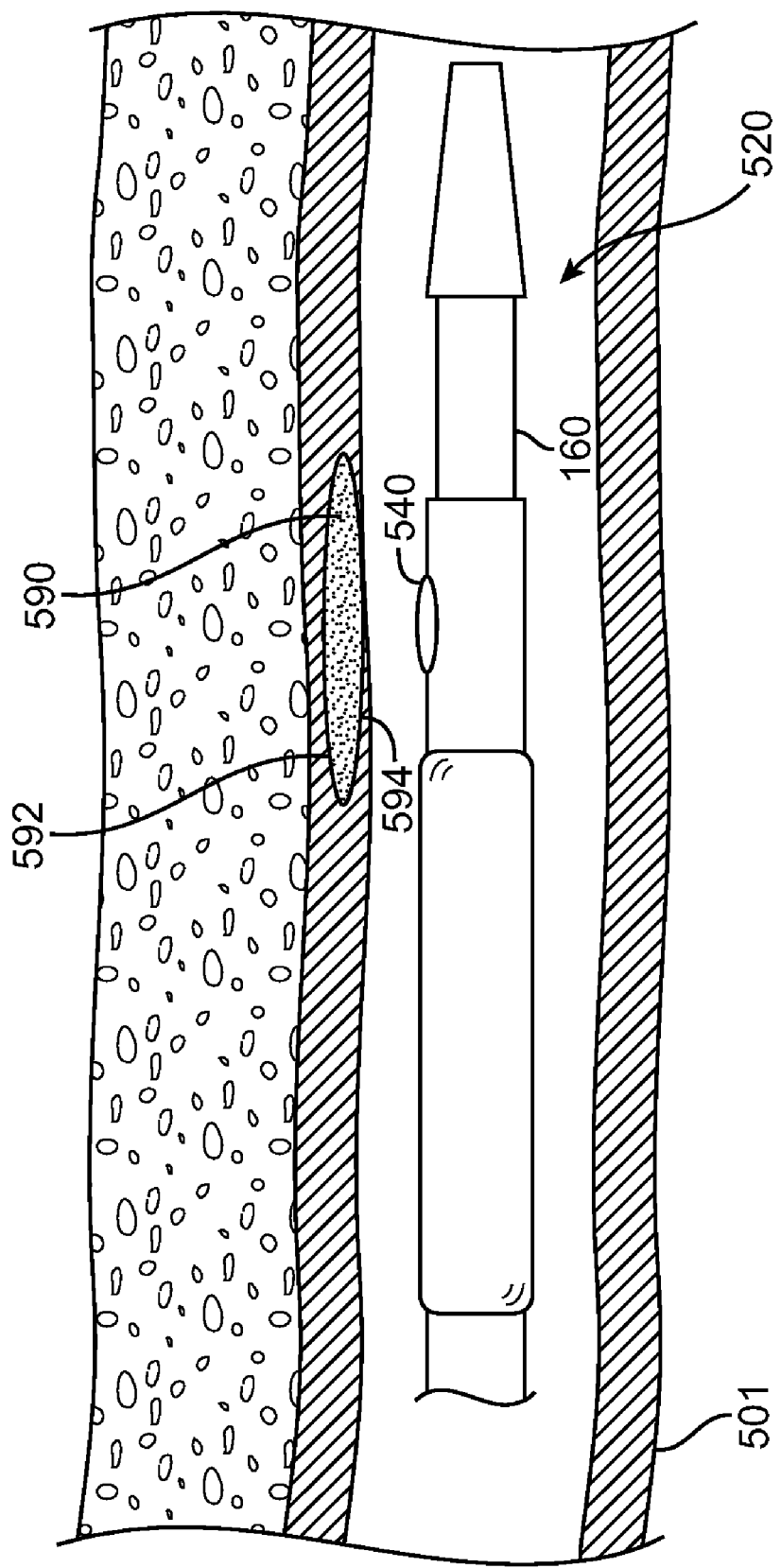
FIGS. 5A to 5F illustrates another embodiment of a method of treating a vulnerable plaque using the system illustrated in FIG. 1, in accordance with the present invention.
Figure 5B:
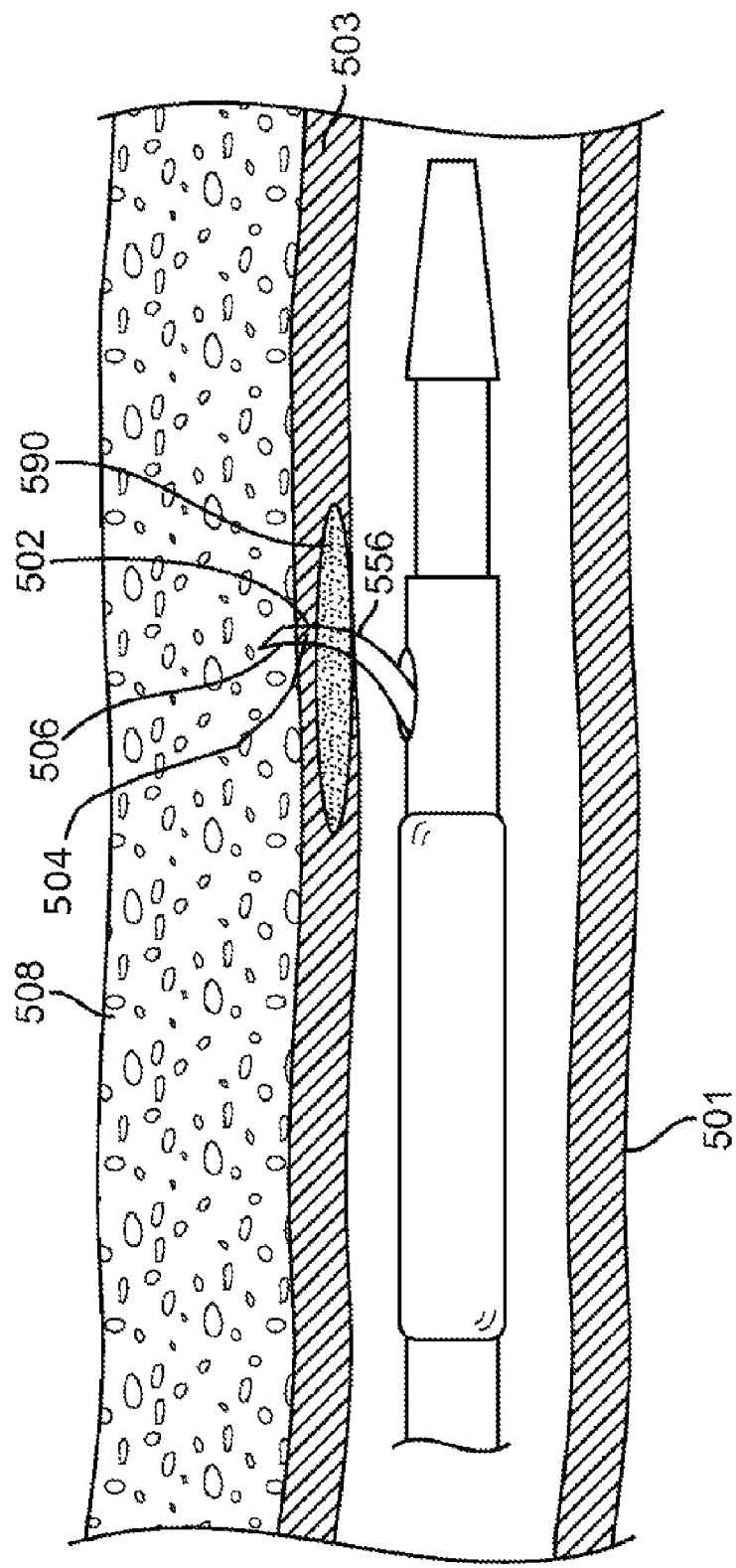

As shown in FIG. 5A, a distal end of a treatment catheter 520 having a tissue penetrating device is advanced to a treatment site within vessel 501 (Block 1115). The treatment site and the vulnerable plaque 590 may be located and visualized using imaging device 160. After determining the location of the vulnerable plaque, side port 540 is oriented towards the fibrous cap 594 of vulnerable plaque 590 having core material 592 (Block 1120). In one embodiment, at least one radiopaque marker disposed on catheter 520, may be used to allow in situ visualization and proper advancement, positioning, and deployment of the tissue penetrating device.

Figure 5C:
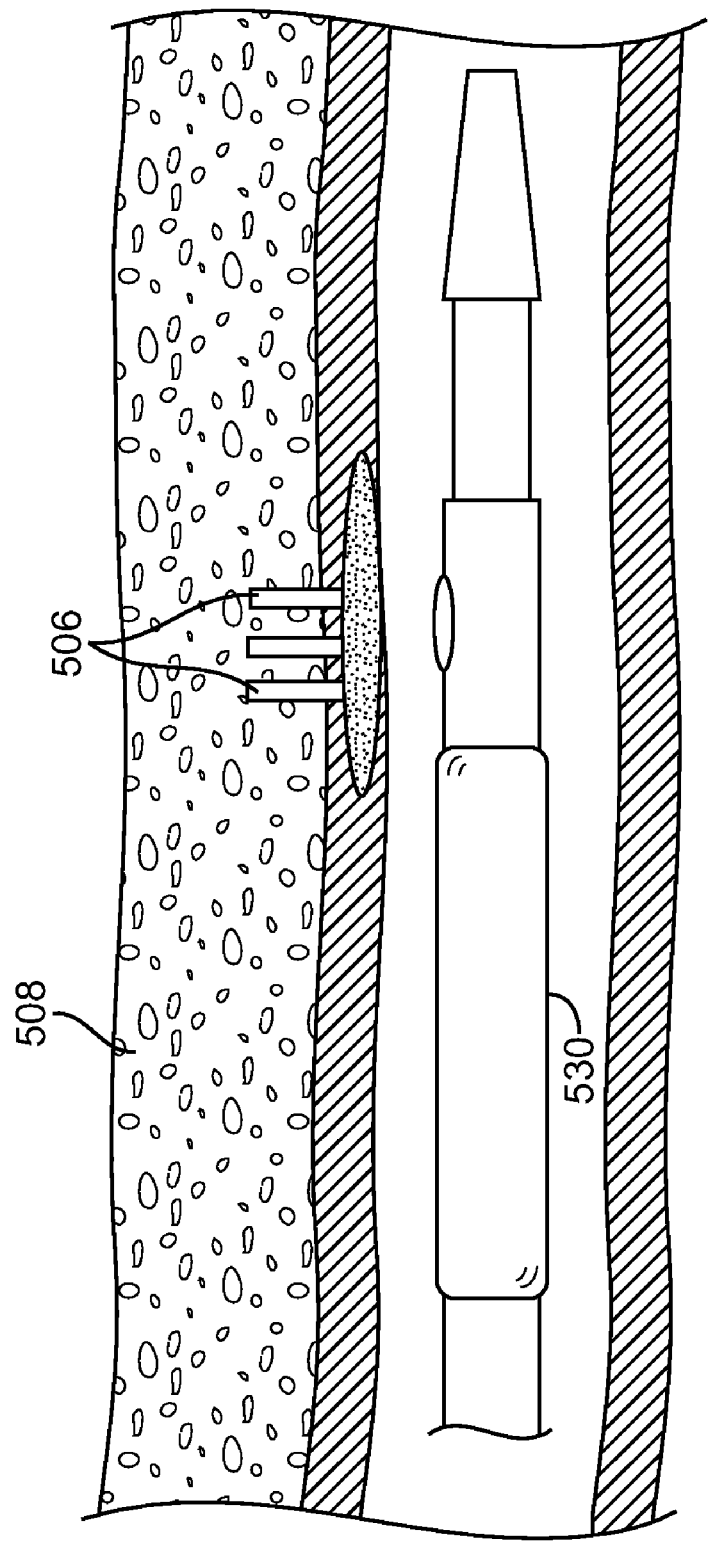

Next, the tissue penetrating device is distally advanced to deploy tissue penetrating portion 556 out of side port 540 (Block 1125) to penetrate the fibrous cap 594 and core material 592 (Block 1130). Tissue penetrating device is further advanced so that tissue penetrating portion 556 penetrates an outer portion 502 of vessel wall 503 to create vessel wall opening 504 and pocket 506 within tissue 508 (Block 1135). The number and placement of the pockets within the tissue adjacent the vulnerable plaque may vary depending on such factors as the dimensions of the vulnerable plaque, the size (gauge) of the tissue penetrating portion and the type and thickness of the tissue adjacent the vessel. Steps 1125 to 1135 may be repeated to create additional pockets. To create additional pockets, the tissue penetrating portion 556 is retracted into catheter 520 and the catheter is advanced to a desired location. At this new location, the tissue penetrating device is deployed as described above to create an additional pocket. The retraction and redeployment of the tissue penetrating portion is continued to create the desired number of pockets. FIG. 5C illustrates three pockets 506 formed within tissue 508. Once the desired number of pockets are formed the tissue penetrating portion is retracted (Block 1140).

Figure 5D:
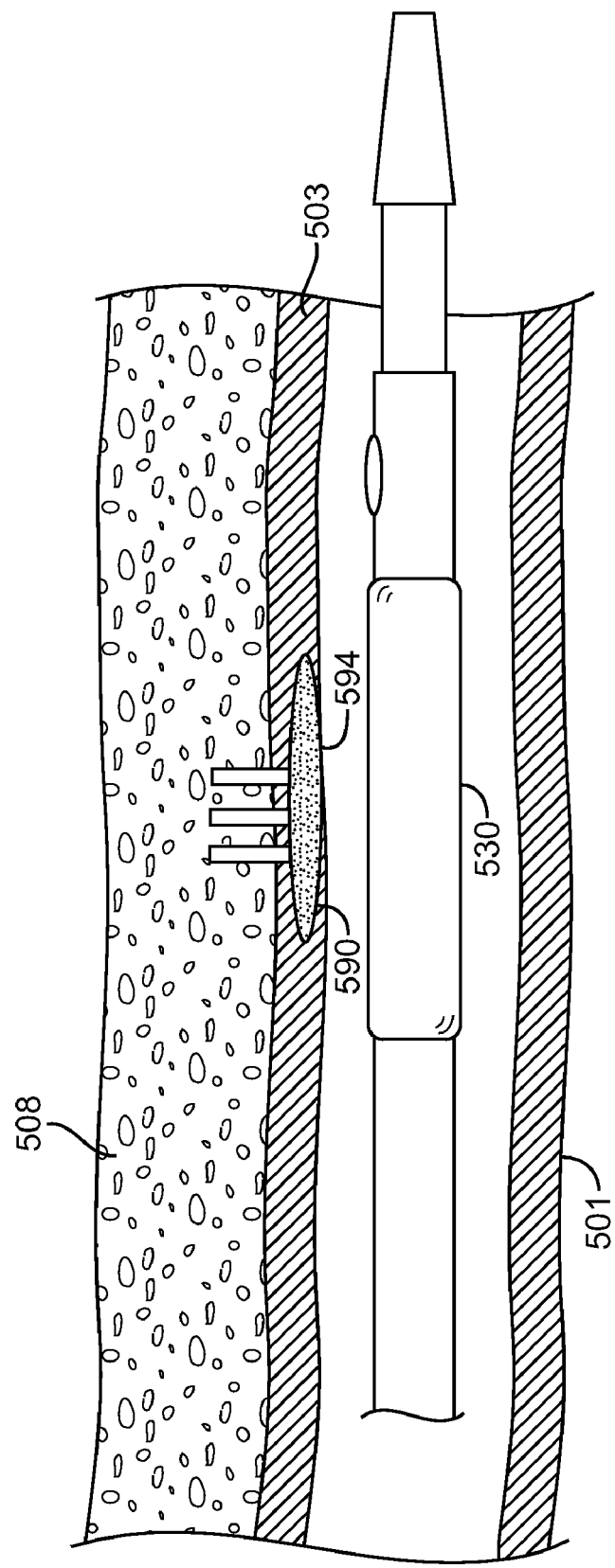
Figure 5E:
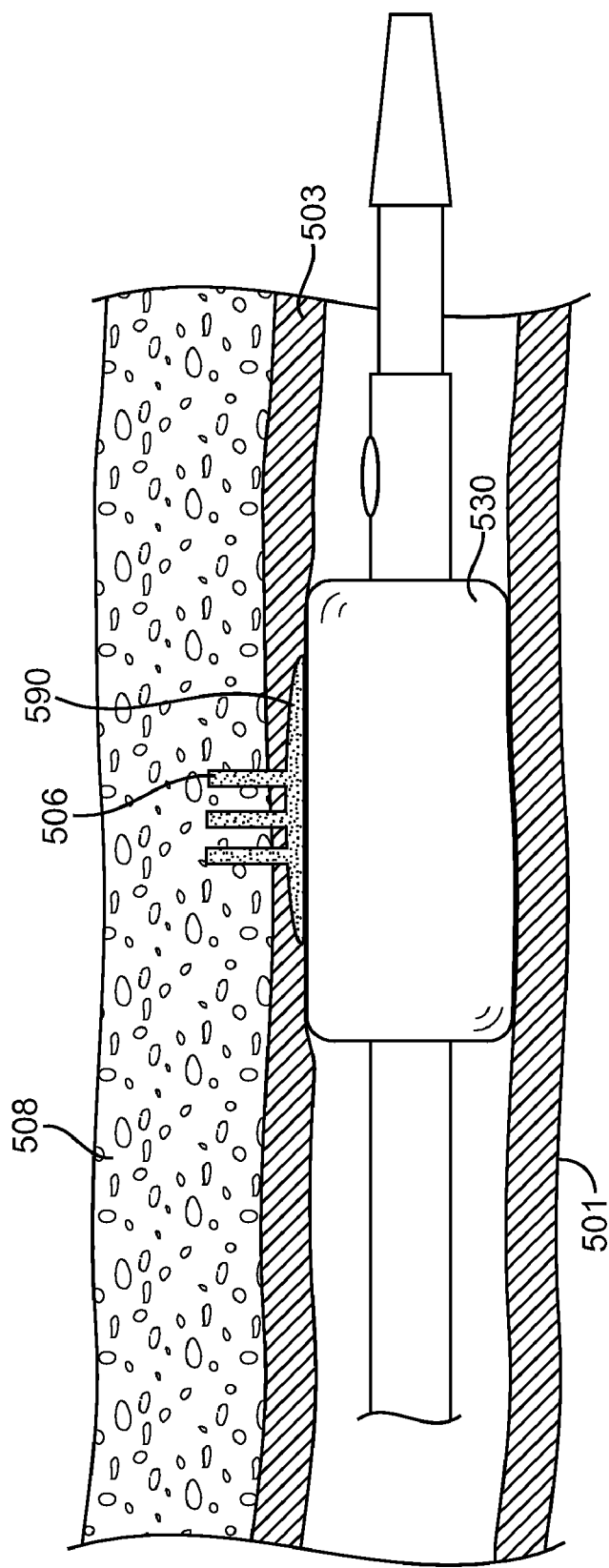
Figure 5F:
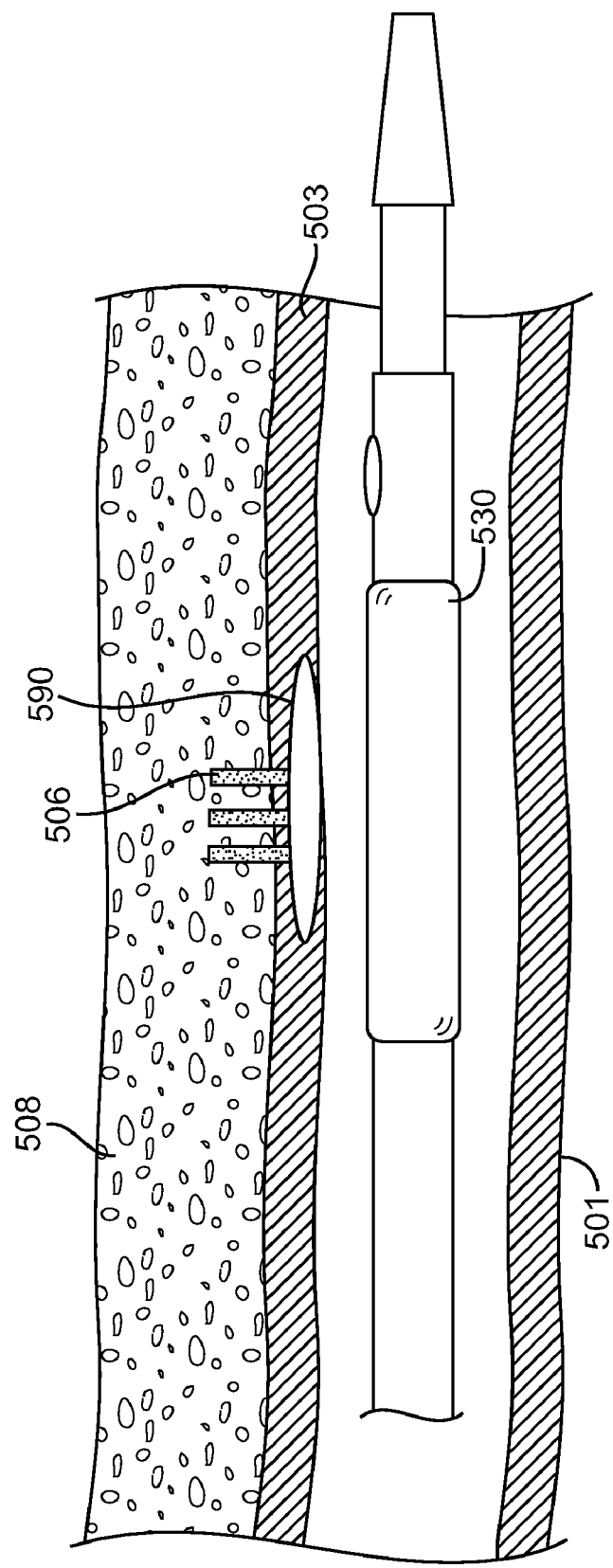

Next, shown in FIG. 5D, catheter 520 is advanced to place balloon 530 adjacent the fibrous cap 594 of vulnerable plaque 590 (Block 1145). Balloon 530 is inflated to exert pressure on the fibrous cap 594 (Block 1150), shown in FIG. 5E. The pressure exerted on fibrous cap 594 forces the core material contained within the vulnerable plaque out vessel wall openings 504 within vessel wall 503. The core material is expelled through opening 504 and into pockets 506 (Block 1155). The material expelled into pockets 506 can be absorbed by the body. The expulsion of the core material into the pockets may be visualized using an imaging device. Upon expulsion of the core material into pocket 506, balloon 530 is deflated as shown in FIG. 5F, and the catheter is removed from the body or advanced to another treatment site as determined by the clinician (Block 1160). Method 1100 ends at 1165 and may be repeated as necessary.

FIGS. 6A to 6D illustrate another embodiment of a system 600 for performing method 1100 for treating a vulnerable plaque, in accordance with the present invention. Specifically, FIGS. 6A to 6D illustrate another embodiment of a tissue penetrating portion 656 for forming pockets in tissue adjacent a vulnerable plaque. In this embodiment, tissue penetrating portion 656 includes a pocket forming expandable device 670. Tissue penetrating portion 656 includes a closed tip and at least one side opening 675 for inflating an expandable pocket forming device 670. In this embodiment, the at least one side opening 675 is in fluid communication with a fluid source (not shown) via a lumen within the tissue penetrating device that extends from opening 675 to a proximal end of the tissue penetrating device.

In use, the distal tip 629 of system 600 is advanced to a treatment site and side port 640 is oriented toward vulnerable plaque 690. The method of advancing system 600 to the treatment site and orienting side port 640 may be the same as or similar to that described above for Block 1115 and Block 1120, respectively.

Next, the tissue penetrating device is distally advanced to deploy tissue penetrating portion 656 out of side port 640 to penetrate the fibrous cap 694 and core material 692 (see, Blocks 1125 and 1130). Tissue penetrating device is further advanced so that tissue penetrating portion 656 penetrates an outer portion 602 of vessel wall 603 (see, Block 1135) to create vessel wall opening 604. Continued advancement of the tissue penetrating device places tissue penetrating portion 656 within tissue 608 adjacent vulnerable plaque 690.

Figure 6B:
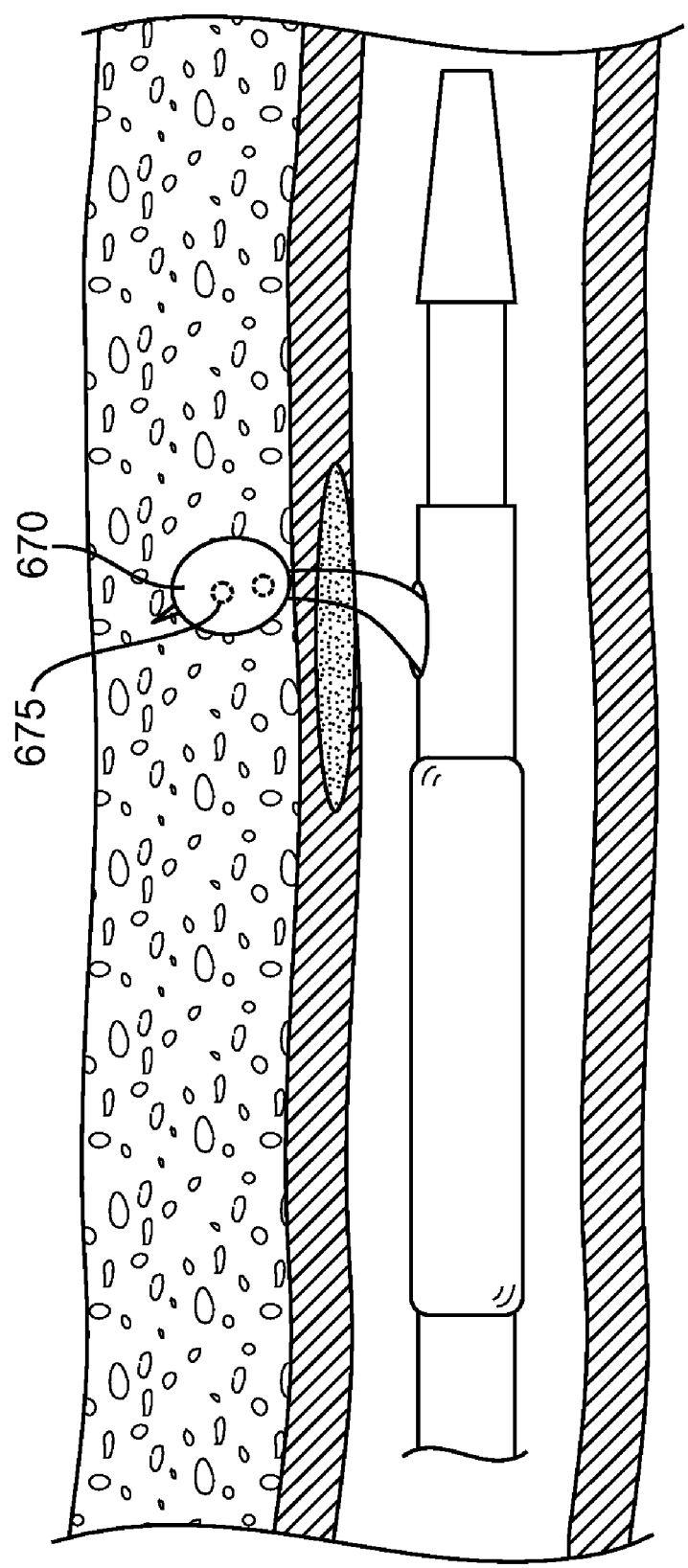

Next, as shown in FIG. 6B, a pocket is created by inflating expandable pocket forming device 670. The expansion of device 670 forms a pocket 606 approximately the same size as the outer periphery of inflated pocket forming device 670. After forming pocket 606, pocket forming device 670 is deflated and tissue penetrating portion 656 is retracted. Following retraction of tissue penetrating portion 656, catheter 620 is advanced to place balloon 630 adjacent the fibrous cap 694 of vulnerable plaque 690 (see, Blocks 1140 and 1145).

Figure 6C:
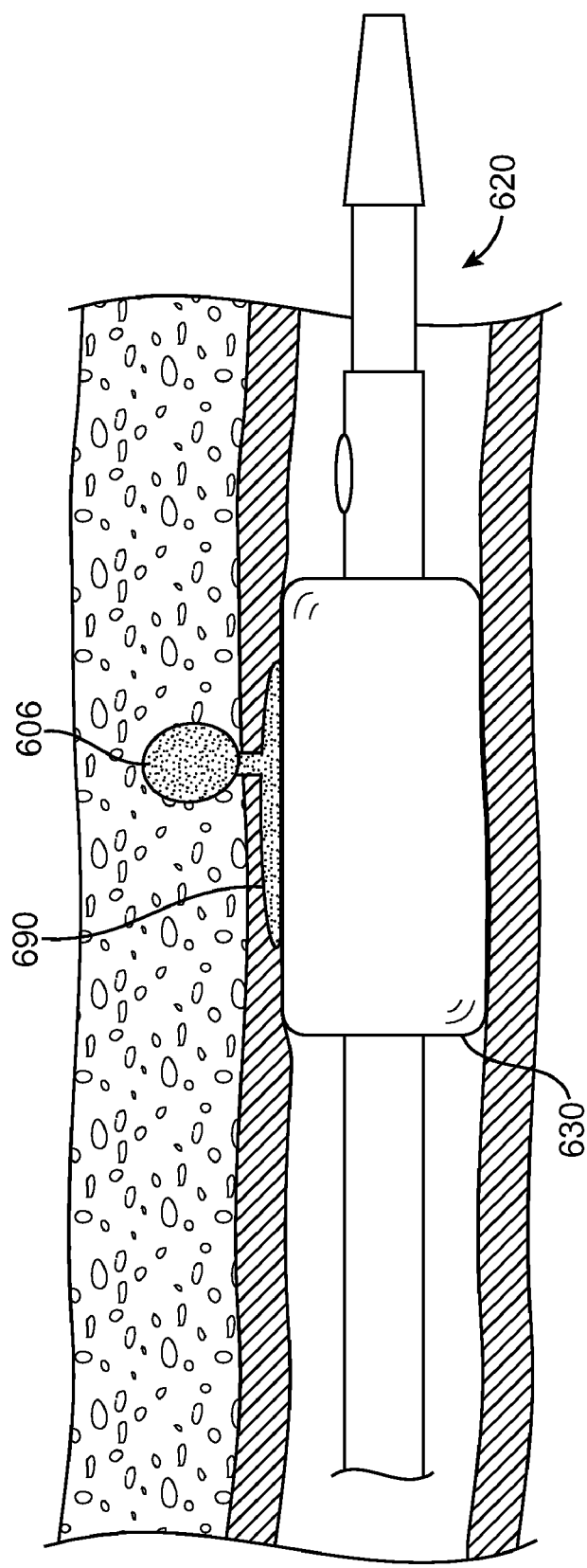
Figure 6D:
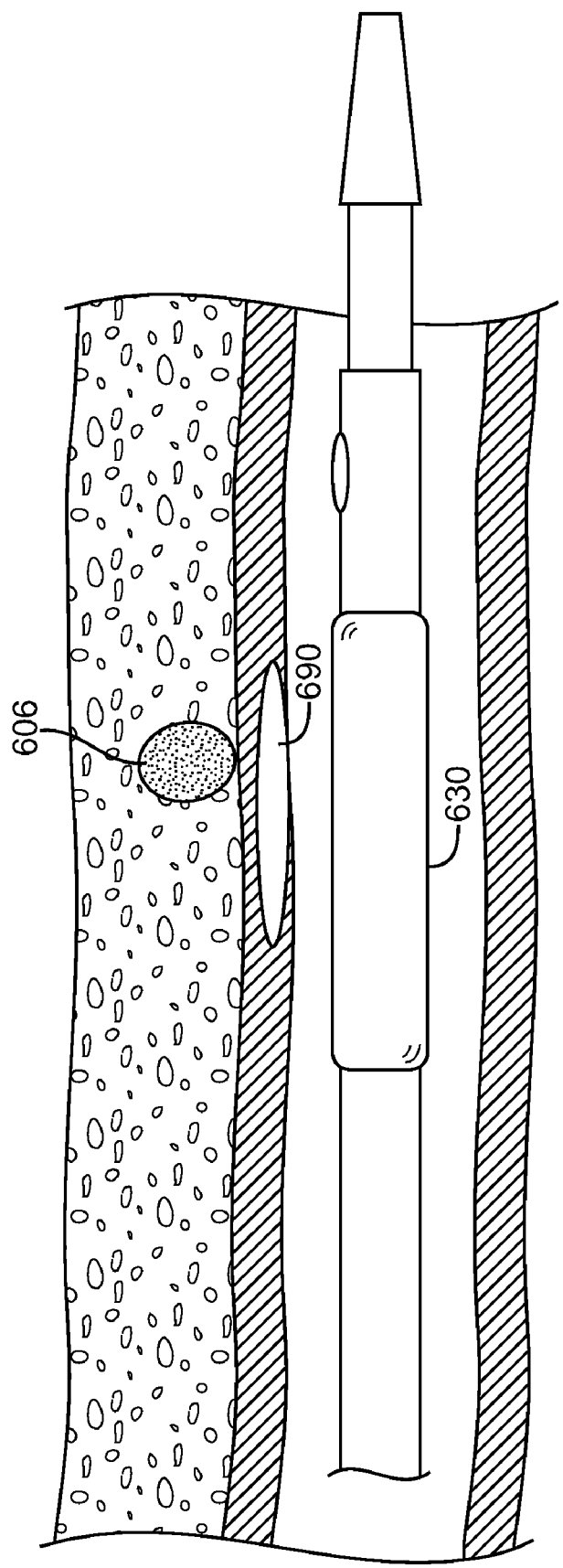

As shown in FIG. 6C, balloon 630 is inflated to exert pressure on the fibrous cap 694 (see, Block 1150). The pressure exerted on fibrous cap 694 forces the core material contained within the vulnerable plaque out vessel wall openings 604 within vessel wall 603. The core material is expelled through opening 604 and into pocket 606 (see, Block 1155). The material expelled into pocket 606 can be absorbed by the body. The expulsion of the core material into the pockets may be visualized using an imaging device. Upon expulsion of the core material into pocket 606, balloon 630 is deflated as shown in FIG. 6D, and the catheter is removed from the body or advanced to another treatment site as determined by the clinician (see, Block 1160).

FIGS. 7A to 7D illustrate another embodiment of a system 700 for performing method 1100 for treating a vulnerable plaque, in accordance with the present invention. Specifically, FIGS. 7A to 7D illustrate another embodiment of a tissue penetrating portion 756 for forming pockets in tissue adjacent a vulnerable plaque. In this embodiment, tissue penetrating portion 756 includes a closed tip and at least one side opening 775 for ejecting fluid into tissue surrounding tissue penetrating portion 756. The ejection of fluid forms a pocket for receiving expelled core material. In this embodiment, the at least one side opening 775 is in fluid communication with a fluid source (not shown) via a lumen within the tissue penetrating device that extends from opening 775 to a proximal end of the tissue penetrating device.

In use, the distal tip 729 of system 700 is advanced to a treatment site and side port 740 is oriented toward vulnerable plaque 790. The method of advancing system 700 to the treatment site and orienting side port 740 may be the same as or similar to that described above for Block 1115 and Block 1120, respectively.

Next, the tissue penetrating device is distally advanced to deploy tissue penetrating portion 756 out of side port 740 to penetrate the fibrous cap 794 and core material 792 (see, Blocks 1125 and 1130). Tissue penetrating device is further advanced so that tissue penetrating portion 756 penetrates an outer portion 702 of vessel wall 703 (see, Block 1135) to create vessel wall opening 704. Continued advancement of the tissue penetrating device places tissue penetrating portion 756 within tissue 708 adjacent vulnerable plaque 790.

Figure 7A:
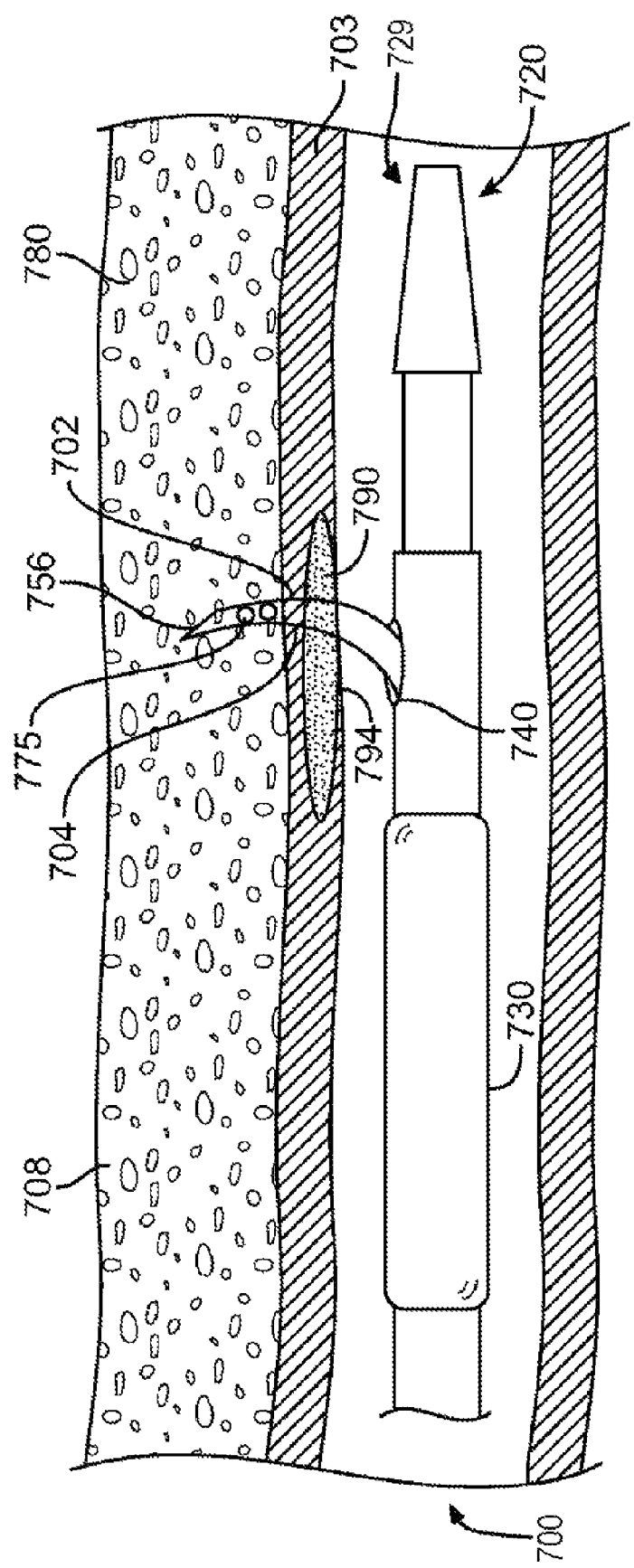
FIGS. 7A to 7D illustrates another embodiment of a method of treating a vulnerable plaque using the system illustrated in FIG. 1, in accordance with the present invention.
Figure 7B:
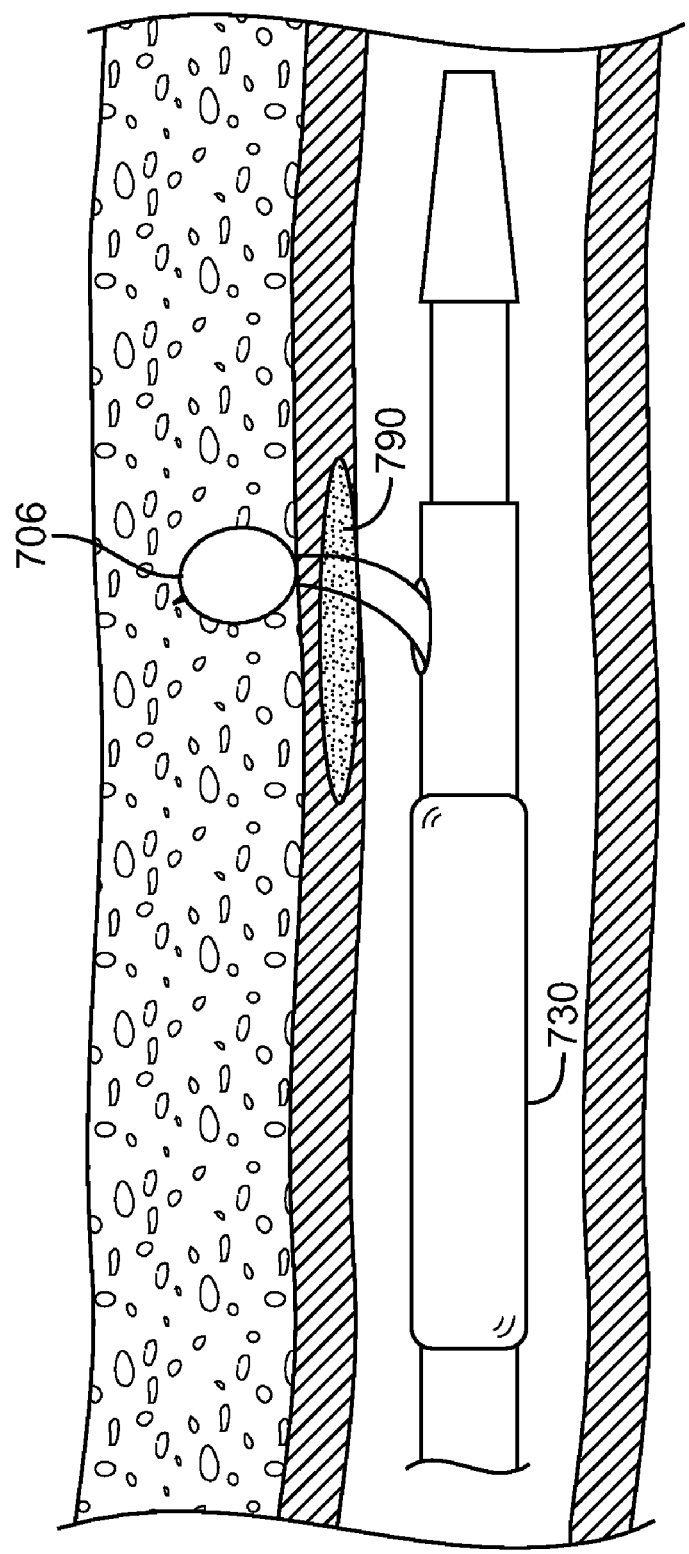
Figure 7C:
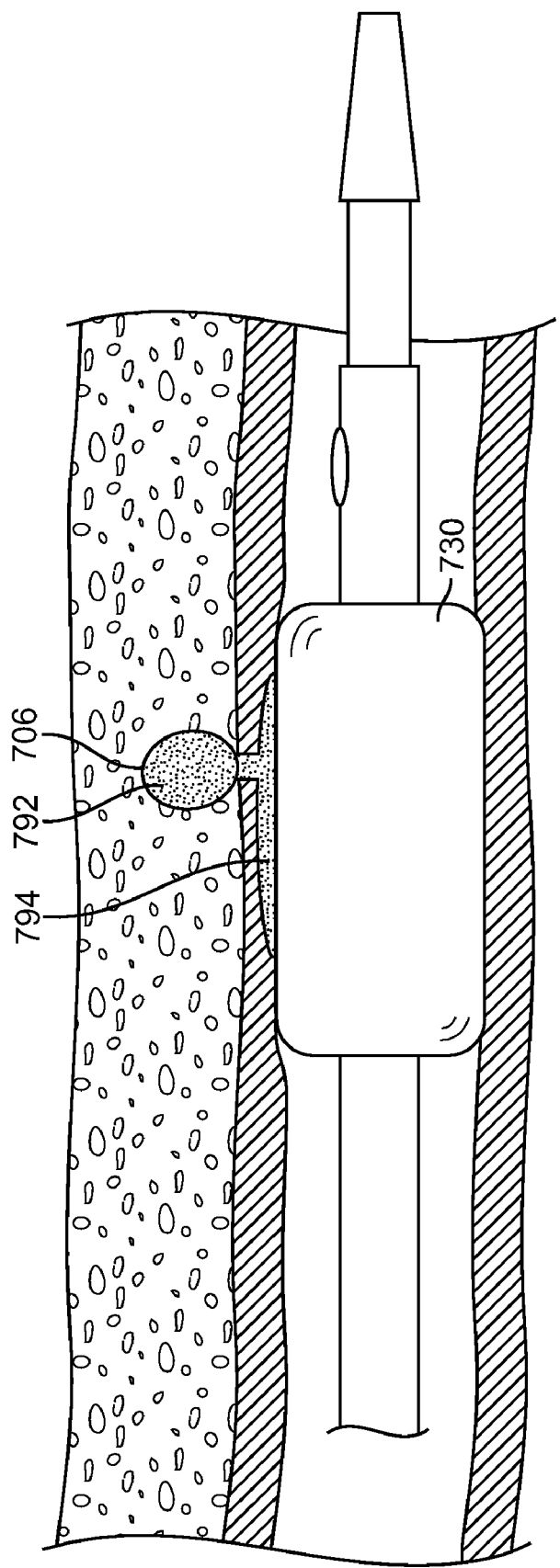

Next, as shown in FIG. 7B, a pocket 706 is created by ejecting fluid from the at least one side opening 775. After forming pocket 706, tissue penetrating portion 756 is retracted. Following retraction of tissue penetrating portion 756, catheter 720 is advanced to place balloon 730 adjacent the fibrous cap 794 of vulnerable plaque 790 (see, Blocks 1140 and 1145).

Figure 7D:
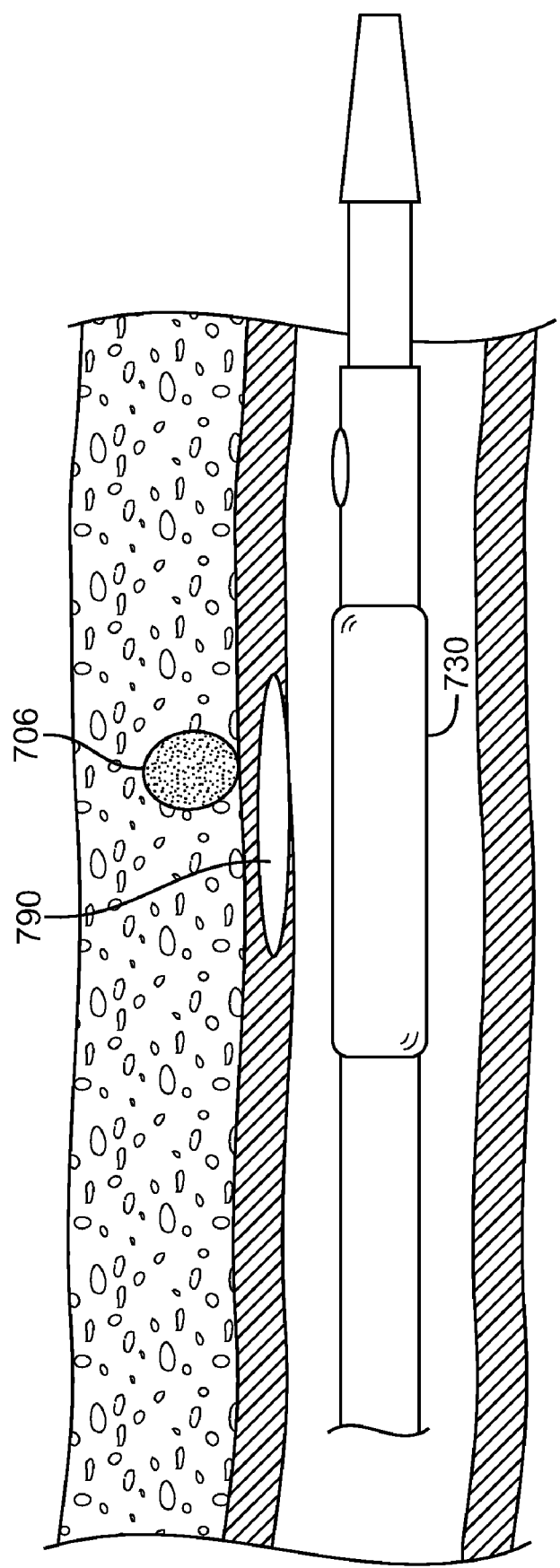

As shown in FIG. 6C, balloon 730 is inflated to exert pressure on the fibrous cap 794 (see, Block 1150). The pressure exerted on fibrous cap 794 forces the core material contained within the vulnerable plaque out vessel wall openings 704 within vessel wall 703. The core material is expelled through opening 704 and into pocket 706 (see, Block 1155). The material expelled into pocket 706 can be absorbed by the body. The expulsion of the core material into the pockets may be visualized using an imaging device. Upon expulsion of the core material into pocket 706, balloon 730 is deflated as shown in FIG. 7D, and the catheter is removed from the body or advanced to another treatment site as determined by the clinician (see, Block 1160).

Figure 8:
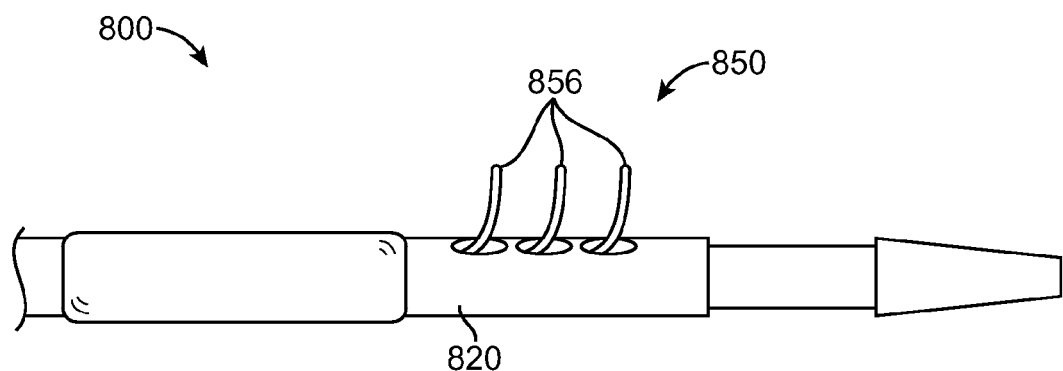
FIG. 8 illustrates one embodiment of a tissue penetration device for use in the methods for treating a vulnerable plaque, in accordance with the present invention.

FIG. 8 illustrates another embodiment of a tissue penetrating device 850 of a system 800, made in accordance with the present invention. In this embodiment, tissue penetrating device has a plurality of tissue penetrating portions 856, in this case, three disposed upon a distal end of tissue penetrating device 850 in a serial manner. System 800 further includes a plurality of side ports 840, one side port for each tissue penetrating portion 856. Those with skill in the art will appreciate that the number of tissue penetrating portions and corresponding side ports 840 may vary depending on such factors as the size of the vulnerable plaque and the desired number of pockets and/or wall openings.

In one embodiment, a proximal end of each tissue penetrating portion is attached to a distal portion of a single elongated tissue penetrating device. In another embodiment, a proximal end of each tissue penetrating portion extends the length of catheter 820 for actuation by the clinician.

Figure 9:
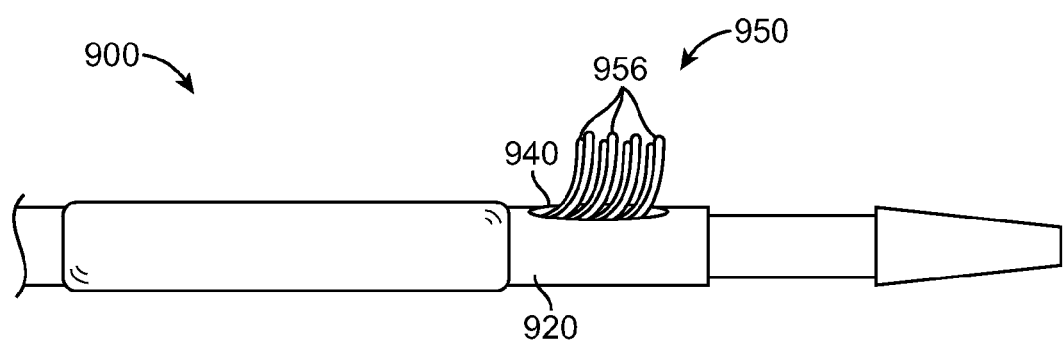
FIG. 9 illustrates another embodiment of a tissue penetration device for use in the methods for treating a vulnerable plaque, in accordance with the present invention.

FIG. 9 illustrates another embodiment of a tissue penetrating device 950 of a system 900, made in accordance with the present invention. In this embodiment, tissue penetrating device has a plurality of tissue penetrating portions 956, in this case, six disposed upon a distal end of tissue penetrating device 950 in a needle array. System 900 further includes a side port 940. A proximal end of each tissue penetrating portion 956 is attached to a distal portion of a tissue penetrating device. Those with skill in the art will appreciate that the number of tissue penetrating portions may vary depending on such factors as the size of the vulnerable plaque and the desired number of pockets and/or wall openings.

In another embodiment, at least one pocket may be formed using an electrically conductive tissue penetrating portion. In one embodiment, tissue penetrating portion is at least partially conductive, for example, by providing an electrode thereon (not shown) or by forming the tissue penetrating portion from a conductive material such as platinum, gold, or possibly stainless steel. A conductor, such as an electrically conductive wire (not shown), may extend proximally from the tissue penetrating portion through a lumen of the tissue penetrating device to the handle. A source of electric current may then be coupled to the conductor to form the pocket in the tissue by ablation.

While the embodiments of the invention disclosed herein are presently considered to be preferred, various changes and modifications can be made without departing from the spirit and scope of the invention. For example, the catheter, inflatable member, and tissue penetrating device are not limited to the illustrated and described embodiments. In addition, the method disclosed for treating a vulnerable plaque may vary. For example, additional steps may be performed in addition to those described.

Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

The invention claimed is:

1. A method of treating vulnerable plaque, the method comprising:
    forming at least one opening through an outer vessel wall, the forming including penetrating a fibrous cap and penetrating a core material of the vulnerable plaque prior to penetrating the outer vessel wall, the at least one opening being in fluid communication with the vulnerable plaque;
    compressing the vulnerable plaque from within the vessel; and
    forcing the core material of the vulnerable plaque through the formed vessel wall opening.

2. The method of claim 1 further comprising:
    forming a pocket in fluid communication with the at least one opening, the pocket disposed within tissue adjacent the at least one opening.

3. The method of claim 2 wherein forcing a core material of the vulnerable plaque through the formed vessel wall opening further comprises expelling the core material into the formed pocket.

4. The method of claim 1 wherein compressing the vulnerable plaque from within the vessel and forcing the core material of the vulnerable plaque through the formed vessel wall opening comprises inflating an expandable device into contact with a fibrous cap of the vulnerable plaque and exerting pressure upon the vulnerable plaque.

5. The method of claim 2 wherein forming a pocket in fluid communication with the at least one opening comprises penetrating a portion of tissue adjacent the vulnerable plaque with a tissue penetrating portion of a tissue penetrating device.

6. The method of claim 2 wherein forming a pocket in fluid communication with the at least one opening comprises penetrating a portion of tissue adjacent the vulnerable plaque with a tissue penetrating portion having an expandable pocket forming device attached thereto and inflating the expandable pocket forming device.

7. The method of claim 2 wherein forming a pocket in fluid communication with the at least one opening comprises penetrating a portion of tissue adjacent the vulnerable plaque with a tissue penetrating portion having at least one side opening, the side opening in fluid communication with a fluid source and ejecting a portion of fluid to form the pocket.

8. A method of treating vulnerable plaque, the method comprising:
    delivering a puncture device to a vulnerable plaque location within a vessel via a catheter;
    puncturing a fibrous cap of the vulnerable plaque and forming at least one opening through an outer vessel wall adjacent the vulnerable plaque;
    removing the puncturing device;
    delivering a compressing device to the punctured vulnerable plaque via a catheter;
    compressing the vulnerable plaque with the compressing device; and
    forcing at least a portion of a core material of the vulnerable plaque through the at least one outer vessel wall opening.

9. The method of claim 8 further comprising:
    forming a pocket in fluid communication with the at least one outer vessel wall opening, the pocket disposed within tissue adjacent the at least one opening.

10. The method of claim 9 wherein forcing at least a portion of a core material of the vulnerable plaque through the formed outer vessel wall opening further comprises expelling the core material into the formed pocket.

11. The method of claim 8 wherein forming at least one opening through an outer vessel wall comprises penetrating a fibrous cap and penetrating the core material of the vulnerable plaque prior to penetrating the outer vessel wall.

12. The method of claim 8 wherein compressing the vulnerable plaque from within the vessel and forcing the core material of the vulnerable plaque through the formed vessel wall opening comprises inflating an expandable device into contact with the fibrous cap of the vulnerable plaque and exerting pressure upon the vulnerable plaque.

13. The method of claim 9 wherein forming a pocket in fluid communication with the at least one outer vessel wall opening comprises penetrating a portion of tissue adjacent the vulnerable plaque with a tissue penetrating portion of a tissue penetrating device.

14. The method of claim 9 wherein forming a pocket in fluid communication with the at least one opening comprises penetrating a portion of tissue adjacent the vulnerable plaque with a tissue penetrating portion having an expandable pocket forming device attached thereto and inflating the expandable pocket forming device.

15. The method of claim 9 wherein forming a pocket in fluid communication with the at least one opening comprises penetrating a portion of tissue adjacent the vulnerable plaque with a tissue penetrating portion having at least one side opening, the side opening in fluid communication with a fluid source and ejecting a portion of fluid to form the pocket.

* * * * *